US009987376B2

(12) United States Patent
Moses

(10) Patent No.: US 9,987,376 B2
(45) Date of Patent: Jun. 5, 2018

(54) DELIVERY SYSTEM FOR DELIVERY OF A SUBSTANCE INTO THE ORAL CAVITY

(75) Inventor: Jonatan Moses, Save (SE)

(73) Assignee: NORINVENT AB, Vetlanda (SE)

( * ) Notice: Subject to any disclaimer, the term of this patent is extended or adjusted under 35 U.S.C. 154(b) by 79 days.

(21) Appl. No.: 13/139,694

(22) PCT Filed: Dec. 21, 2009

(86) PCT No.: PCT/SE2009/051478
§ 371 (c)(1),
(2), (4) Date: Nov. 29, 2011

(87) PCT Pub. No.: WO2010/071593
PCT Pub. Date: Jun. 24, 2010

(65) Prior Publication Data
US 2012/0065160 A1    Mar. 15, 2012

(30) Foreign Application Priority Data
Dec. 19, 2008   (SE) ...................................... 0802632

(51) Int. Cl.
*A61K 31/717* (2006.01)
*A61K 31/702* (2006.01)
*A61K 31/715* (2006.01)
*A61K 31/718* (2006.01)
*C07H 1/00* (2006.01)
*A61K 47/61* (2017.01)

(52) U.S. Cl.
CPC .................................... *A61K 47/61* (2017.08)

(58) Field of Classification Search
CPC ........................... A61K 47/4823; A61K 47/61
USPC ......... 514/61, 54, 57, 60, 1.11; 536/56, 102, 536/123.1
See application file for complete search history.

(56) References Cited

U.S. PATENT DOCUMENTS

| 6,299,904 B1 | 10/2001 | Shimizu et al. |
| 2003/0119761 A1 | 6/2003 | Christian |
| 2004/0116348 A1* | 6/2004 | Chau ................ A61K 47/48215 514/1.3 |
| 2006/0217293 A1 | 9/2006 | Orlando et al. |
| 2007/0031502 A1 | 2/2007 | Pettersson et al. |

FOREIGN PATENT DOCUMENTS

| EP | 1295595 A1 | 3/2003 |
| EP | 1595533 A1 | 11/2005 |
| GB | 2381194 A | 4/2003 |
| JP | H03502920 A | 7/1991 |
| JP | 08-104651 A | * 4/1996 |
| JP | 8-104651 A | 4/1996 |
| JP | 08-104651 A | 4/1996 |
| JP | H08104651 A | 4/1996 |
| JP | H11508565 A | 7/1999 |
| JP | 2008231013 A | 10/2008 |
| JP | 2011542073 A | 8/2015 |
| WO | WO-2007144724 A1 | 12/2007 |
| WO | WO-2008/081463 A2 | 7/2008 |
| WO | WO-2010071593 A1 | 6/2010 |

OTHER PUBLICATIONS

Yoshiyuki et al.; JP 08104651, Apr. 23, 1996 (English Machine Translation).*
"International Application Serial No. PCT/SE09/051478, International Search Report dated Apr. 8, 2010", 7 pgs.
"International Application Serial No. PCT/SE09/051478, Written Opinion dated Apr. 8, 2010", 7 pgs.
"European Application Serial No. 09833756.1, Supplementary European Search Report dated Apr. 23, 2015", 7 pgs.
Notice of Reasons for Rejection mailed by the Japanese Patent Office dated Jan. 18, 2016 for application JP 2015-027914 (Applicant—Norinvent AB // Inventor—Moses) (Original—4 pages // Translation—4 pages).
"International Application Serial No. PCT/SE09/051478, International Preliminary Report on Patentability dated Jun. 21, 2011", 8 pgs.
"Japanese Application Serial No. 2011-542073, Office Action dated Oct. 14, 2014", (w/ English Translation), 5 pgs.

* cited by examiner

*Primary Examiner* — Shaojia Anna Jiang
*Assistant Examiner* — Michael C Henry
(74) *Attorney, Agent, or Firm* — Ballard Spahr LLP

(57) ABSTRACT

A delivery system for use in the oral cavity, the system comprising a carrier for a bioactive substance. The carrier has a surface comprising oxygen-binding sites (X), and at least one link comprising a pentose group and one or more additional sugar groups, the pentose group being bonded to one of said oxygen binding sites (X) and wherein one or more bioactive molecules (R) are bonded directly to one of the sugar groups of the at least one link or to one or more substituents on one or more sugar groups in the at least one link.

17 Claims, 4 Drawing Sheets

DELIVERY SYSTEM FOR DELIVERY OF A SUBSTANCE INTO THE ORAL CAVITY

RELATED APPLICATIONS

This application is a nationalization under 35 U.S.C. 371 of PCT/SE2009/051478, filed Dec. 21, 2009 and published as WO 2010/071593 A1 on Jun. 24, 2010, which claimed priority to Sweden Patent Application No. 0802632-0, filed Dec. 19, 2008; which applications and publication are incorporated herein by reference in their entirety.

TECHNICAL FIELD

The invention pertains to a delivery system for use in the oral cavity, the system comprising a carrier for a bioactive substance.

BACKGROUND

Several problems are known to be associated with per-oral delivery of pharmaceuticals where the pharmaceutical is swallowed and passes through the gastro-intestinal system.

One major problem with per-oral delivery is metabolic breakdown of the pharmaceuticals as they pass through the gastro-intestinal tract. Metabolic processes may cause the drug to break down into non-active or even harmful metabolites. This means that the required therapeutic dose will be unnecessarily large and that unwanted side effects may occur. A further disadvantage is that it is difficult to optimize the dose on an individual basis. In addition, for some pharmaceuticals, metabolic breakdown makes it unsuitable to use oral delivery.

The risk of deliberate or inadvertent overdosing is also a concern as the required therapeutic dose must be higher than the theoretically required dose in order to compensate for metabolic breakdown.

An orally ingested drug will also require a relatively long time before any effect of the drug is noticed. This means that where a quick response is particularly important such as with pain killers or drugs for motion sickness, there is a strong need for a better delivery system.

Nausea and vomiting may also prohibit uptake of a drug when administered orally. Migraines and motion sickness which are accompanied by such symptoms are examples of conditions where it is often too late for ingested drugs to have an effect once the symptoms have set in.

In order to overcome the deficiencies of oral delivery, it has previously been suggested to use injections, or sprays delivered to the oral or nasal cavity. A further alternative method is anal delivery. All these delivery methods suffer from drawbacks such as being technically complicated, unduly expensive, unpleasant, or painful.

Furthermore, it has been proposed to administer pharmaceutical agents by means of tablets which dissolve in the oral cavity and release the pharmaceutical agent. Such a tablet is disclosed in EP 1 295 595 A1. However, tablets disintegrating in the mouth suffer from a considerable drawback in that the uptake rate of pharmaceutical agents through the oral mucosa may be too low and that a smaller or larger proportion of the pharmaceutical agent may be inadvertently swallowed by the treated person. Further, when administering a pharmaceutical agent by means of tablets, the tablets will necessarily contain additional substances such as fillers, flavouring, etc. admixed with the active substance. When the tablets contain a small amount of active substance, it is a problem to achieve uniform distribution of the active substance in the tablets so that all tablets contain the same amount of active substance.

With the tablets in EP 1 295 595 A1, the exact dose that is actually administered on each occasion cannot be controlled. Consequently, there is a risk that the administered dose is too low to have the desired effect on the treated individual or too high if the tablet accidentally contains more active substance than intended. Moreover, problems associated with metabolic breakdown of pharmaceuticals may also occur. In order to alleviate the problem of absorption of the pharmaceutical via swallowed saliva it has been suggested in US2007/0031502 A1 to mix a pharmaceutically active agent with a bioadhesion or mucoadhesion promoting compound.

However, there still remains a need for an improved and simplified delivery system that can be used with a broad range of bioactive substances including such substances that cannot be ingested without suffering metabolic degeneration and that solves the problems of accurate dose delivery even of small doses of bioactive substances.

SUMMARY OF THE INVENTION

In accordance with the invention there is now offered a delivery system for use in the oral cavity, the system comprising a carrier for a bioactive substance. The carrier is a material having a surface comprising oxygen-binding sites (X), and at least one link comprising a pentose group and one or more additional sugar groups, the pentose group being bonded to one of said oxygen binding sites (X) and one or more bioactive substances (R) are bonded directly to one of the sugar groups of the at least one link or to one or more substituents on one or more sugar groups in the at least one link.

The further sugar group or groups on the sugar link may be pentose or hexose as desired.

The invention offers several advantages over previously used drug delivery systems such as ingestion of drugs, injections, anal delivery, spray dose delivery, sublingual tablets and dose inhalation.

When the carrier is placed in the oral cavity and comes into contact with saliva, enzymes in the saliva break the bonds in the sugar link thereby releasing the bioactive substance (R) into the oral cavity. The bioactive substance is released directly into the oral cavity as a bioactive molecule having a sugar group coupled to the bioactive substance (R). The hydrophilic sugar group that is bonded to the active substance (R) acts as a promoter that facilitates permeation and immediate uptake of the bioactive molecules through the mucosal membranes in the oral cavity. Accordingly, the bioactive molecules are directly transported into the blood vessels of the mucosa and transported into the blood stream directly to the brain thus bypassing the gastro-intestinal tract.

As many bioactive substances have a hydrophobic character, they are generally not taken up through the hydrophilic oral mucosa or are taken up only at a very low rate such that a large proportion of the administered dose is lost to swallowing of the bioactive substance before it can permeate the mucosa. With the delivery system in accordance with the invention, the risk of loosing active substance to swallowing is eliminated due to the release mechanism which is activated by saliva when the non-dissolving carrier with the active substance is placed in contact with the oral mucosa so that the release takes place exactly where intended. Furthermore, the permeation promoting effect of the hydrophilic sugar group in the bioactive molecule released from the carrier ascertains rapid and almost complete uptake of the released substance regardless of whether it is hydrophilic or hydrophobic. Generally, as much as 98% or more of the active substance will be taken up through the oral mucosa.

Due to the hydrophilic character imparted to the substance-carrying bio-molecule and also due to the high precision in the administration of the active substance, the delivery system according to the invention allows for a wider range of bioactive substances to be administered orally than has been possible with the previously known tablets and compositions that merely dissolve and release the substance in the oral cavity.

The carrier itself is not dissolved in the oral cavity but stays intact and remains in place in contact with the mucosa until it is removed after the treatment has been completed.

Saliva is produced in the salivary glands. The human saliva contains 98% water, but it also contains substances, including electrolytes, mucus, antibacterial compounds and various enzymes.

There are three major enzymes and some minor enzymes found in saliva:
   a) α-amylase. Amylase starts the digestion of starch and lipase fat before the food is even swallowed.
   b) Lysozyme. Lysozyme acts to cause lysis in bacteria.
   c) Lingual lipase. Lingual lipase has a pH optimum of ca. 4.0 which means that it will not be activated until it enters an acidic environment.
   d) Minor enzymes include salivary acid phosphatases A+B, N-acetylmuramyl-L-alanine amidase, NAD(P)H dehydrogenase-quinone, salivary lactoperoxidase, superoxide dismutase, glutathione transferase, class 3 aldehyde dehydrogenase, glucose-6-phosphate isomerase, aldehyde dehydrogenase and tissue kallikrein.

All enzymes in saliva that are able to break down sugars and bonds to substituents on sugar chains contribute to the release function of the invention. Additional enzymes are continuously being discovered and it is expected that the list of known enzymes will be expanded in the future.

The delivery system in accordance with the invention makes it possible to use considerably lower doses than with per-oral delivery without loosing effect of the active component. In comparison with drugs that are swallowed, when using the drug delivery system according to the invention the doses may be reduced to as much as 1/10 of a swallowed dose. The delivery mechanism is quick, highly effective, simple and painless and involves only bio-compatible components and substances such as sugars that even when broken down produce metabolites which are harmless to the human body. Any substituents on the sugar links or on the carrier materials according to the invention should also be chosen so that they produce only non-toxic metabolites.

The delivery system according to the invention is superior to conventional sublingual tablets or other intraorally placed delivery devices that are designed to dissolve in the oral cavity. The delivery system in accordance with the invention can be made to precision to carry and transfer a well-defined and very low dose of a bioactive substance. The carrier structure is placed in the oral cavity and will stay in its intended place, without dissolving or otherwise deteriorating until it is eventually removed by the treated individual or a care-taker after the treatment has been completed. Once the biomolecules consisting of the sugar group coupled to the bioactive substance are released from the carrier they will immediately be transported into the oral mucosa as a result of the hydrophilic character of the sugar group. Consequently, the risk of loosing any of the bioactive substance to inadvertent swallowing is eliminated.

In accordance with the invention, the sugar links on the carrier can be designed with regard to their length, branching and substituents to specifically bind to one or more bioactive substances. It is also possible to create bonds that may be broken by means of additives thus allowing further possibilities of designing the sugar links in order to obtain a higher degree of control of the release mechanism.

The length of the sugar links may vary from the simplest links containing only the carrier-binding pentose and a single additional sugar group to longer and more complex sugar chains. The length of the sugar links determines the amount of bioactive substance or substances that can be bonded to the carrier. For bulky molecules, longer chains are preferably used in order to obtain sufficient spacing from the surface of the carrier and between individual molecules coupled to the link.

The sugar links may be monosaccharides, disaccharides, etc. but are preferably non-branched oligosaccharides or polysaccharides.

A particularly preferred sugar link is a sugar chain consisting of: xylose—galactose—galactose—glucose amine. The link is bonded with the xylose-end to the carrier. A sugar link of this kind is highly bio-compatible as it is naturally occurring in the connective tissue of animals and humans where it acts as a promoter for transporting hydrophobic molecules through biological membranes. When a carrier having such links bonded thereto is placed in the oral cavity, the enzymes in the saliva will start breaking off the sugar groups from the free end of the chain. Accordingly, the first bond that will be broken is the bond between the glucose amine and the following galactose group. If a bioactive substance is bonded to the glucose amine, the resulting bioactive molecule will be composed of the bioactive substance and the glucose amine with the glucose amine constituting a hydrophilic end on the bioactive molecule.

Such sugar links may be obtained from proteoglycans isolated from connective tissue such as connective tissue from cows or pigs. Proteoglycans are compounds comprising a core protein and one or more sugar chains covalently attached, usually via a serine residue. If desired, the protein can be removed from the serine residue by using a proteinase before separating the sugar links from the serine. The sugar links may be enzymatically released from the proteoglycans by subjecting an aqueous solution of the proteoglycans to treatment with a chondritinase and subsequent separation of the sugar links from the solution by centrifugation. When the bond between the serine group and the sugar chain is broken by the chonditrinase, the xylose group at the end of the chain is simultaneously opened up, the oxygen in the resulting xylitol group thereby being exposed to preferential binding to an oxygen binding group such as a nitro-group on the surface of a carrier.

If desired, the biologically derived sugar links may be shortened using chondritrinases to obtain links having fewer sugar groups following on the initial xylose. The chondritrinases are enzymes that are specific for different sugars.

Proteoglycans and their composition are disclosed in Moses et al, 1997 a, 1997, b, 1998, and 1999, a and b (Doctoral Dissertation, Medical Faculty of Lund University, titled "Biosynthesis of the Proteoglycan Decorin, published 1999)

A further way to obtain sugar links for use in the invention is by synthetization. By synthesizing the sugar links, they can be designed to have any composition and length desired. The synthesized sugar links may be bound to a carrier having oxygen binding groups by opening a terminal pentose group for instance with a an aqueous solution of sodium borate, $NaBH_4$ or by treatment with an aqueous NaCl solution as is well known in the art. Apart from the initial pentose, the additional sugar groups may be any pentose or hexose.

When preparing the carrier with the sugar links according to the invention, the reactions are preferably carried out at a pH of 5.6 or lower.

In the oral cavity, the bonds in the sugar links will be broken by enzymes which are present in the saliva of most human beings. Notable exceptions are individuals suffering from Sjögren's Syndrome who lack the right kind of amylase and thereby are unable to break down the sugar links. Other conditions changing the saliva content or affecting saliva production may also affect the enzyme activity. Such conditions may, for instance, be caused by medication, by trauma or by tumours.

However, the delivery system according to the invention will not be completely inefficient even for persons suffering from an enzyme deficiency as the bonds in the sugar links will break apart at low pH, such as at a pH below approximately 5.6. A lowering of the pH in the oral cavity to levels sufficient to break up the sugar links will often take place after a meal and will lead to a release of the bioactive substance from the delivery system.

The delivery system according to the invention has several advantages over prior art delivery systems such as tablets, injections, etc. A major advantage is that it is easy to interrupt the treatment when the desired effect has been achieved by simply removing the carrier from the oral cavity. This means that medication can be tailored on an individual basis.

Furthermore, the risk of overdosing is virtually non-existing as the carrier with the bioactive substance can be removed from the oral cavity at any time. Moreover, because of the superior target effect of the delivery system according to the invention, the dose needed to obtain the desired effect of the bioactive substance is so low that it is impossible to obtain harmful levels of the substance.

The invention can be used with all kinds of drugs and substances acting on the central nervous system and triggering a signal from the brain. Accordingly, locally acting drugs are not suitable for delivery by means of the system according to the invention unless the drug is active locally in the oral cavity. Moreover, drugs that are broken down by saliva such as paracetamol are not suitable for delivery by means of the system according to the invention. A prerequisite is that the bioactive molecule has an active group that is capable of forming a bond to the sugar link. CNS-acting drugs are found among opioid agonists and opioid antagonists, butyrophenones, benzodiazepines. Further drugs are those having effects on the cardiovascular and renal vascular systems.

Some specific examples of drugs that are suitable for delivery by means of the invention are drugs for treating motion sickness, such as scopolamine or citalopram. Further examples are pain relievers such as ibumetin, codeines, morphines and tramadoles, antihypertensives, antiarrhythmics, psychopharmaceuticals, centrally acting diuretics, bronchodilators, etc.

The carrier may be a cellulose-based carrier such as nitrocellulose or a starchbased carrier. The starch may be synthetically, biochemically or biosynthetically derived. Further suitable carriers are collagen, gelatine, elastine or other bio-molecules that are able to form similar matrixes. Cellulose-based carriers and starch-based carriers are preferred as they are low-cost, readily available materials. The carrier material preferably stays inert in the oral cavity and does not dissolve or otherwise deteriorate at least for the duration of the treatment.

Due to the highly efficient delivery of an active substance obtained with the delivery system according to the invention, the carrier with the sugar links and the active substance may be very small and still contain a sufficient dose of the active substance. In order to facilitate handling of the carrier when placing it in the oral cavity and removing it after treatment, the carrier may be provided on or in a handling device. Accordingly, the carrier may be attached to a material having a practical size. Without limitation, the physical form of the delivery system may be a film, a pad, a patch, a pellet, a tape, etc. to which the carrier has been attached. It is also conceivably to use micro-beads, etc. contained in a saliva permeable wrapping.

The delivery system may further comprise drug enhancers and/or permeability facilitators and/or flavours.

BRIEF DESCRIPTION OF DRAWINGS

The invention will be described in detail with reference to the attached figures. It is to be understood that the drawings and diagrams are designed solely for the purpose of illustration and are not intended as a definition of the limits of the invention, for which reference should be made to the appended claims.

In the drawings.

DETAILED DESCRIPTION OF THE INVENTION

Example 1

In order to show the effect of the delivery system comprising a carrier with bonded sugar links in accordance with the invention, as compared to a carrier without sugar links, the following tests were performed.

Figure 1:
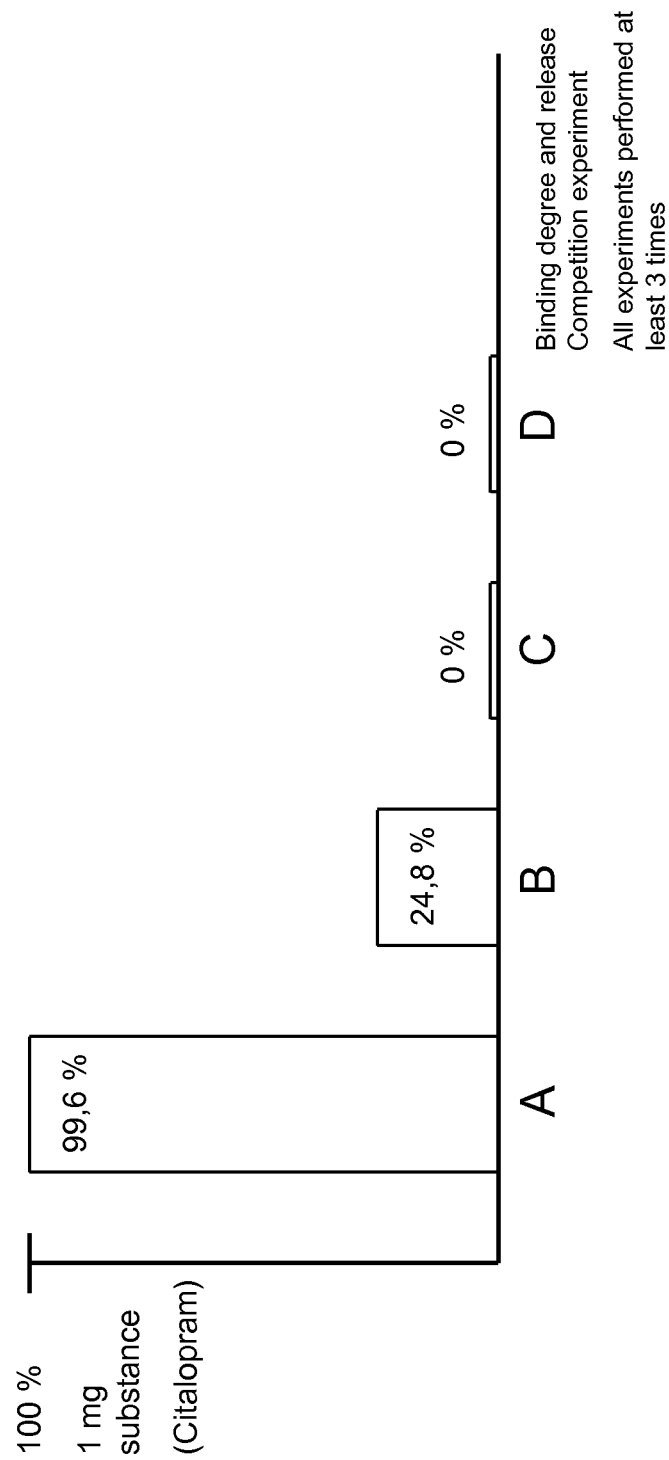
FIG. 1 is a diagram showing the results of a comparative test.

The test results are shown in the diagram in FIG. 1. In the tests, the bioactive substance was citalopram and the carrier was a nitrocellulose-matrix carrier with and without sugar chains bonded to the carrier. All carriers in samples A, B, C and D were treated with the same amount of active substance (R) in relation to the carrier surface. The substance-treated carriers were subsequently subjected to treatment with salivary enzyme to recover any substance that had been bound to the carriers.

Tests performed with other substances such as scopolamine and ibumetinols showed similar results to those in FIG. 1.

Column A in the diagram in FIG. 1 illustrates binding of citalopram to a nitrocellulose/sugar-link carrier according to the invention. The carrier was saturated with citalopram implying that all available bond sites were occupied by citalopram, as shown by a more than 99.6% recovery of citalopram when released again by treatment with salivary enzyme. Accordingly, virtually all citalopram was recovered from the nitrocellulose/sugar chain membrane.

Column B shows binding of citalopram directly to a nitrocellulose carrier without any sugar links. As is seen in FIG. 1, only approximately 24.8% of the citalopram was recovered when treating the carrier with salivary enzyme. This test shows that the carrier material itself, without the sugar links has a limited ability to bind the substance.

Column C shows the result of an attempt to bind and release substance from a nitrocellulose/sugar-chain carrier having the sugar links blocked by pre-saturation with another substance. A useful way of pre-saturating the membrane is by means of methylating the sugar groups in the sugar links.

Column D shows a comparative test performed only with a pre-saturated nitrocellulose carrier, without any sugar links coupled thereto.

The tests demonstrate that when all potential bond sites on the carriers were blocked, no citalopram was absorbed or otherwise taken up by the carriers as evidenced by the fact that no substance was subsequently recovered from the carriers.

Example 2

Example 2 was performed to show the effect of in vivo release of scopolamine when using a delivery system according to the invention.

Figure 2:
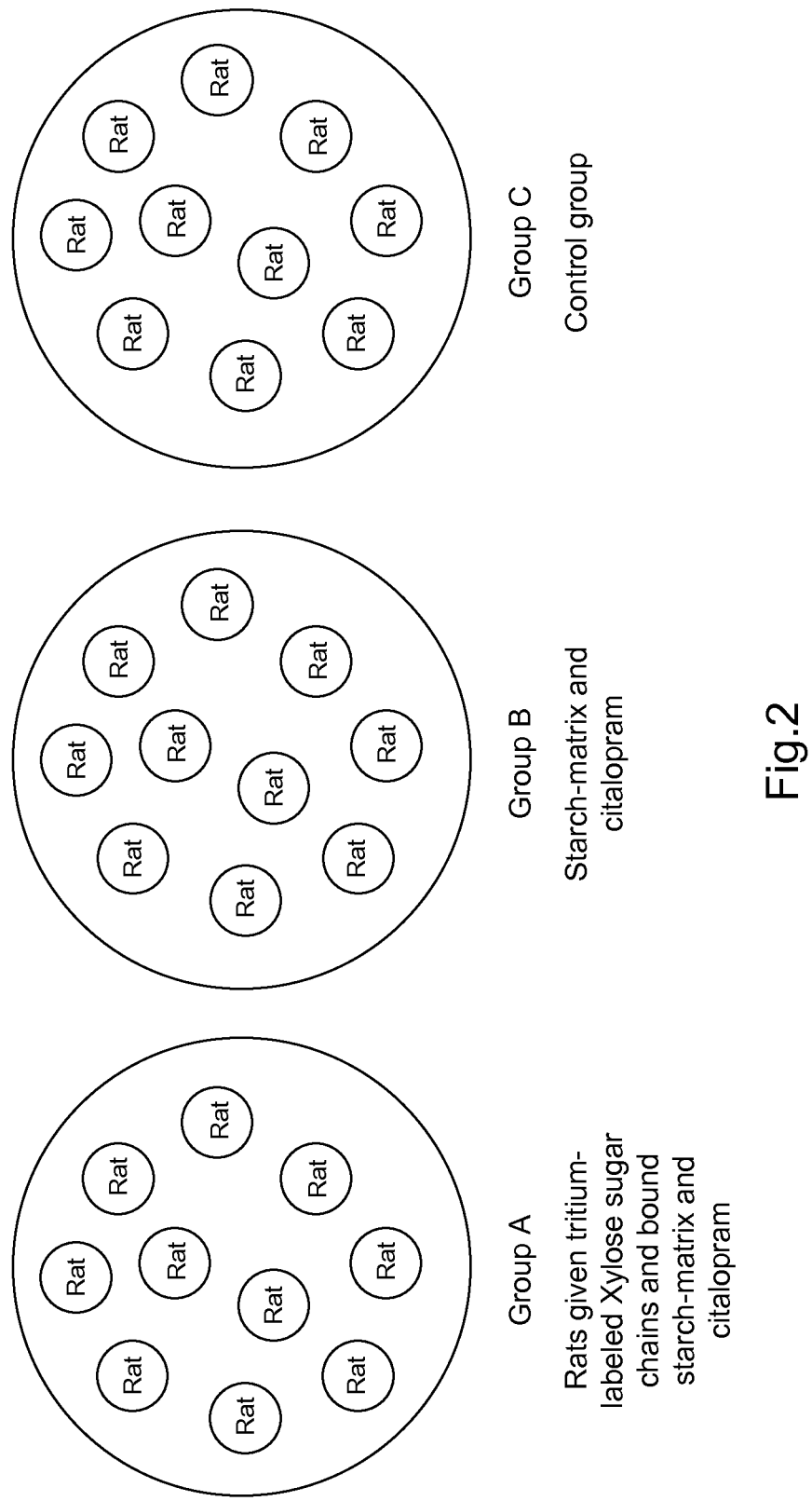
FIG. 2 shows test groups A, B and C according to a first example.

White/white laboratory standard rats were used for the tests. The animals were divided into three test groups A, B, C with 10 rats in each group, as shown in FIG. 2. In test group A, the rats were given scopolamine. The active substance was bound to sugar chains which in turn were bound to a simple starch matrix in accordance with the invention. The matrix had been fixated in a column and the sugar chains had been labelled with tritiated xylose as described in Moses et al, 1997 a, 1997, b, 1998, and 1999, a and b (Doctoral Dissertation, Medical Faculty of Lund University, titled "Biosynthesis of the Proteoglycan Decorin, published 1999) allowing the sugar chains to be subsequently traced within the rat body.

Group B served as a control and was treated with uncoupled scopolamine and a starch matrix carrier without sugar chains.

Group C received no carrier or active substance.

All rats where checked for normal salivary production and rat saliva was also tested (not shown) to establish ability to release the compound from the sugar carrier.

The membrane size was 1×1 mm made out of starch. To this the labelled sugar chains were coupled and one membrane was put under the upper lip of each rat.

Three equally calibrated centrifuges were used in the test, one for each group of rats A, B, C. Each centrifuge was placed in a box having an entrance/exit through which the rats could move freely between their cage and the centrifuge box. The rats were first allowed to find their way into the centrifuge box before they were lifted up and placed in the centrifuge.

The rats were subsequently spun in the centrifuges at 3 G during 30 seconds.

After centrifugation, the ability of each group A, B, C to localize the exit in the centrifuge box and to return to the cage as well as general steadiness were observed.

Group A, who had received ⅒ of a normal dose of scopolamine bond to a carrier according to the invention showed no change in normal behaviour such as signs of motion sickness and managed to directly locate the exit in the centrifuge box.

Group B, who had been given the same amount of substance, but without the substance being bound by the sugar chain to the matrix showed clear signs of motion sickness and could not find the exit during the test period of 1 h.

Group C, who received neither matrix nor substance, behaved in a similar manner as described for group B.

The test was repeated with new groups A, B and C but with citalopram instead of scopolamine. The results of the second test were similar to the results of the first test. Accordingly, the group A rats were not affected by centrifugation while the group B and C rats showed clear signs of motion sickness.

The rats were terminated by carbon-dioxide 4 h after centrifugation and the intestinal organs were examined. The presence of scopolamine or citalopram in the rat bodies was detected by spectrophotometrics and digital imaging as described in Goncalves, Diaz and Moses et al.

In group A, the kidneys contained less than 0.1%, the liver less than 0.2% and the brain 99% of the active substance. The remainder of the drug was dispersed throughout other parts of the body.

Group B had less than 4% active substance in the brain, over 75% in kidney or liver and the rest dispersed throughout the body.

As expected, group C had no active substance found anywhere.

The results where identical for scopolamine and citalopram, showing that the substance itself has no targeting effect.

Example 3

A further test was performed on voluntary humans.

Figure 3:
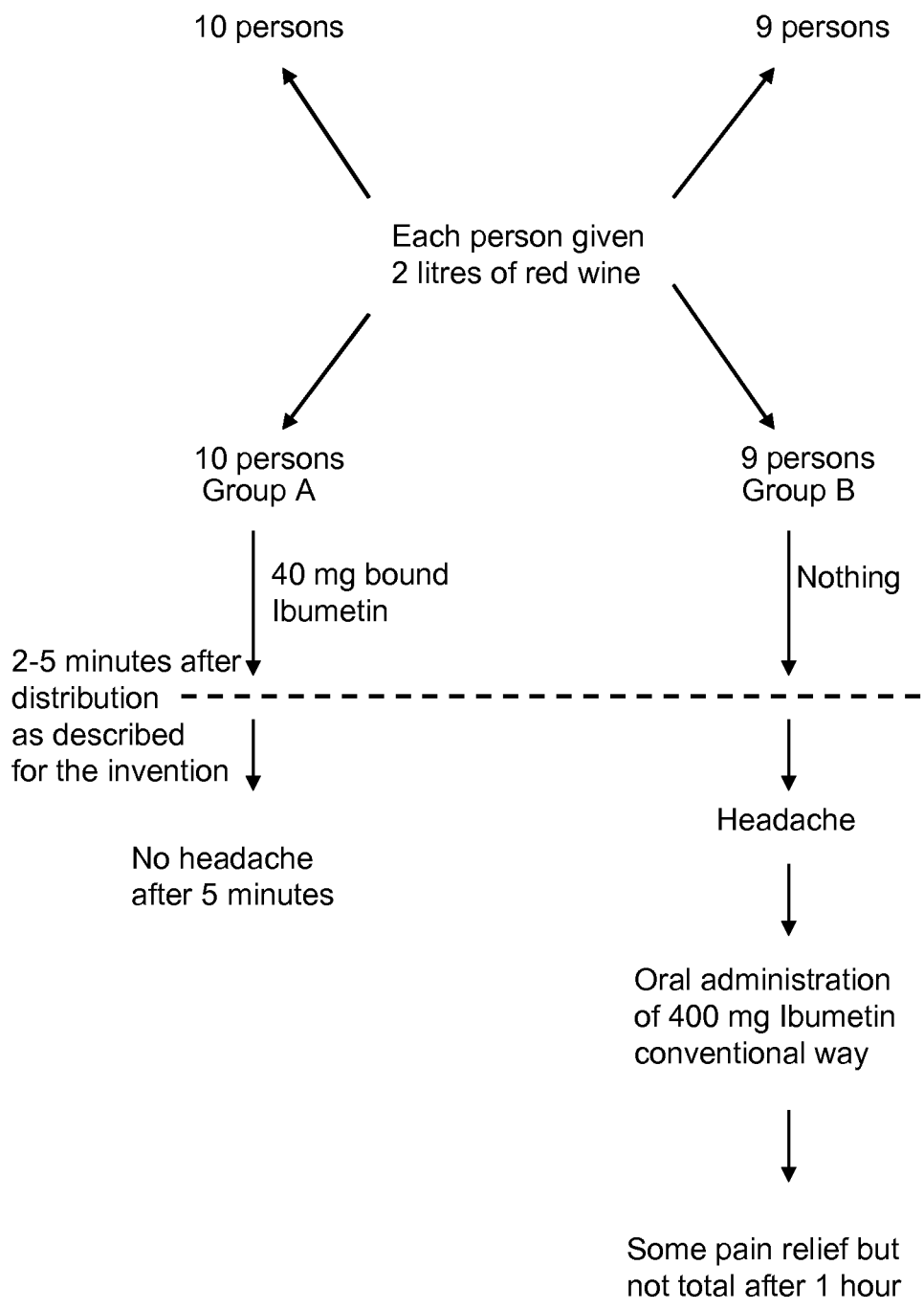
FIG. 3 shows a diagram of a test procedure according to a second example.

The test was performed on a group of 19 persons. Each test person was given 2 L of red wine without gender discrimination. The wine was consumed during 3 hours the evening before testing. The following morning the individuals were divided into two groups A and B, respectively. Group A received 40 mg (⅒ of a normal orally administered dose) of ibumetine bonded to a carrier according to the invention. Group B where given an empty membrane with only sugar chains and no active substance. Group A felt a total relief of the headache caused by the red wine within 5 minutes, whereas group B felt no relief at all from the bare membrane with sugar chains. Group B where therefore treated with 400 mg ibumetine by conventional oral delivery. Various degrees of relief were noted after 45 min-1 h. The test procedure is diagrammatically illustrated in FIG. 3.

Accordingly, the experiments showed that the delivery system according to the invention is fast-acting and accurate. Moreover, the released substance is rapidly taken up through the oral mucosa and is transported directly to the brain without metabolic loss of substance.

Figure 4:
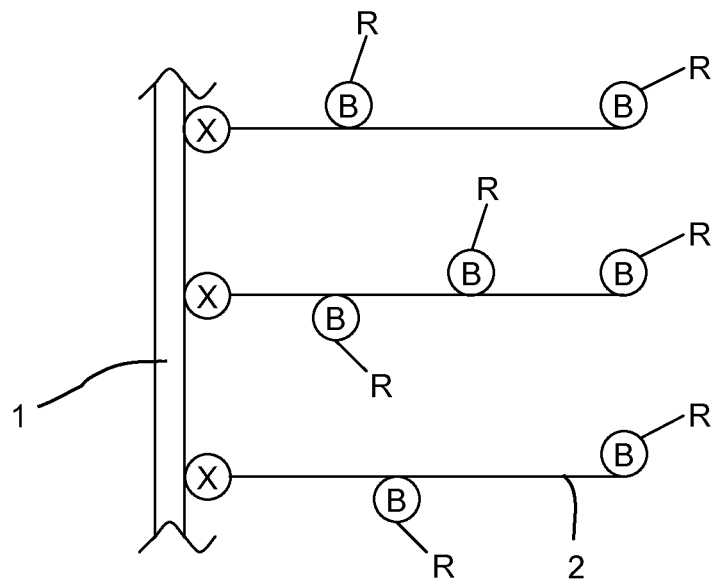
FIG. 4 shows an example of a carrier surface with sugar links.

FIG. 4 shows schematically the structure of a carrier (membrane) 1, having sugar links 2, bonded to oxygen binding sites (X) on the carrier 1. The oxygen binding sites (X) may be P, C, S or N. The sugar links have substituents such as OH, NH, $SO_4$ or $PO_4$, forming bond sites (B) for bonding a bioactive substance (R) to the sugar links.

The carrier may be any non-toxic material exhibiting oxygen-binding groups and may be cellulose-based or starch based. The starch may be synthetically, biochemically or biosynthetically derived. Further suitable carriers are collagen, gelatine, elastine or other bio-molecules that are able to form similar matrixes. Cellulose-based carriers, such as nitrocellulose are preferred for being low-cost readily available materials. The carrier is preferably substantially non-soluble or non-dissolvable in saliva, at least during a time period corresponding to an expected period of treatment.

In accordance with the invention, the bond sites (B) on the sugar links 2 have a bioactive substance R bonded thereto. The bioactive substance may be any pharmaceutical or other substance acting on the central nervous system and triggering a signal from the brain, as set out herein.

The sugar links may comprise one or more sugar groups. Depending on the number of bond sites (B) that are desired and the size and stereochemistry of the bioactive molecules bonded to the sugar chain, specific sugar links can be designed for each purpose.

When put in the oral cavity of a healthy individual, the salivary enzymes will act on the sugar chains and break the bonds between the sugar groups, thus releasing the bonded bioactive molecules comprising a sugar moiety and a bioactive substance (R) in the oral cavity where the bioactive molecules can be directly taken up through the mucosa as described herein.

The invention claimed is:

1. A delivery system for use in the oral cavity, the system comprising a carrier that is substantially non-soluble in saliva for a bioactive substance, wherein the carrier that is substantially non-soluble in saliva comprises a cellulose-based material that is substantially non-soluble in saliva or a starch-based material that is substantially non-soluble in saliva and has a surface comprising oxygen-binding sites, and in that the system comprises at least one link covalently or non-covalently bonded to the carrier that is substantially non-soluble in saliva, said at least one link comprising two or more sugar groups, wherein one or more bioactive substances (R) are bonded directly to a first sugar group of the two or more sugar groups or to one or more substituents on the first sugar group of the two or more sugar groups of the at least one link, wherein the at least one link is a non-branched oligosaccharide or polysaccharide, wherein the at least one link has a first end and a second end, wherein the first end is covalently or non-covalently bonded to an oxygen binding site on the carrier that is substantially non-soluble in saliva, wherein the first end is terminated with a second sugar group of the two or more sugar groups, wherein the second sugar group of the two or more sugar groups is a pentose group, wherein the at least one link comprises at least one substituent selected from the group consisting of OH, NH, $NH_2$, $SO_4$ and $PO_4$, constituting a bonding site (B) for the one or more bioactive substances (R), and wherein the delivery system has a physical form of a film, a pad, a patch, or a tape.

2. A delivery system according to claim 1, wherein the oxygen binding sites on the carrier that is substantially non-soluble in saliva are selected from the group consisting of: P, C, S and N.

3. A delivery system according to claim 1, wherein the carrier that is substantially non-soluble in saliva comprises nitrocellulose.

4. A delivery system according to claim 1, wherein the at least one link has a second end terminated with a glucose amine.

5. A delivery system according to claim 4, wherein the at least one link is a sugar chain with the formula: xylose-galactose-galactose-glucose amine.

6. A delivery system according to claim 1, wherein the first end of the at least one link is covalently bonded to the oxygen binding site on the carrier that is substantially non-soluble in saliva.

7. A delivery system according to claim 1, wherein the first end of the at least one link is non-covalently bonded to the oxygen binding site on the carrier that is substantially non-soluble in saliva.

8. A delivery system according to claim 1, wherein the at least one link comprises at least one substituent being $NH_2$, constituting a bonding site (B) for the one or more bioactive substances (R).

9. A delivery system according to claim 6, wherein the at least one link comprises at least one substituent being $NH_2$, constituting a bonding site (B) for the one or more bioactive substances (R).

10. A delivery system according to claim 7, wherein the at least one link comprises at least one substituent being $NH_2$, constituting a bonding site (B) for one or more bioactive substances (R).

11. A method for releasing a bioactive substance into the oral cavity comprising the step of placing the delivery system of claim 1 in the oral cavity of an individual, wherein the delivery system of claim 1 is arranged to release the one or more bioactive substances (R) upon contact with salivary enzymes present in the oral cavity of the individual.

12. A method according to claim 11, wherein the enzymes from the saliva break a bond between the two or more sugar groups in the at least one link thereby releasing at least one bioactive molecule comprising the one or more bioactive substances (R) bonded to the first sugar group from the at least one link.

13. A method for producing the delivery system of claim 1 comprising the steps of:
   a) providing a carrier that is substantially non-soluble in saliva having a surface exhibiting oxygen-binding sites (X);
   b) covalently or non-covalently bonding at least one link to the carrier that is substantially non-soluble in saliva, the at least one link having a first end and comprising two or more sugar groups and wherein the second sugar group being pentose of the two or more sugar groups is covalently or non-covalently bonded to one of said oxygen binding sites (X); and
   c) bonding one or more bioactive substances (R) directly to the first sugar group of the two or more sugar groups or to one or more substituents on the first sugar group of the two or more sugar groups in the at least one link, thereby producing the delivery system of claim 1.

14. The method according to claim 13, wherein bonding of the at least one link to the carrier that is substantially non-soluble in saliva is carried out in an aqueous solution having a pH of 5.6 or lower.

15. A method according to claim 13, wherein the oxygen binding sites (X) on the carrier that is substantially non-soluble in saliva are selected from the group consisting of P, C, S and N.

16. A method according to claim 13, wherein the carrier that is substantially non-soluble in saliva comprises nitrocellulose.

17. A method according to claim 14, wherein the at least one link is a non-branched oligosaccharide or polysaccharide.

* * * * *